(12) United States Patent
Tsikas

(10) Patent No.: US 6,613,937 B2
(45) Date of Patent: Sep. 2, 2003

(54) S-NITROSO- AND S-NITRO-N-ACYL-L-CYSTEINE ESTER DERIVATIVES AS PHARMALOGICALLY ACTIVE AGENTS AND PHARMACEUTICAL COMPOSITIONS CONTAINING SAID COMPOUNDS

(76) Inventor: Dimitrios Tsikas, Drosselweg 21, 30974 Wennigsen (DE)

( * ) Notice: Subject to any disclaimer, the term of this patent is extended or adjusted under 35 U.S.C. 154(b) by 141 days.

(21) Appl. No.: 10/016,453

(22) Filed: Oct. 30, 2001

(65) Prior Publication Data

US 2002/0091102 A1 Jul. 11, 2002

Related U.S. Application Data

(63) Continuation of application No. PCT/EP00/03934, filed on May 2, 2000.

(30) Foreign Application Priority Data

Apr. 30, 1999 (DE) .......................................... 199 19 941

(51) Int. Cl.$^7$ ............................................ C07C 321/00
(52) U.S. Cl. ........................ 560/149; 560/147; 560/12; 514/550
(58) Field of Search ................................ 560/147, 149, 560/12; 514/550

(56) References Cited

U.S. PATENT DOCUMENTS 5,187,305 A 2/1993 Thompson et al.

OTHER PUBLICATIONS

Tsikas, Dimitrios & Ful Biochem and Biophys. Research Communication (1996) 220 (3) 939–44.*

Bonnett et al., "Nitrosation and Nitrosylation of Haemoproteins and Related Compounds. Part 2. The Reaction of Nitrous Acid with the Side Chains of alpha–Acyl–Amino–Acid Esters," *Journal of the Chemical Society—Perkin Transactions 1*, 8, pp. 1969–1974 (1979).

Petit et al., "Novel Donors of Nitric Oxide Derived of S–Nitrosocysteine Possessing Antioxidant Activities," *Brazilian Journal of Medical and Biological Research*, 32, pp. 1407–1412 (1999).

Tsikas et al., "Investigations of S–Transnitrosylation Reactions between Low– and High–Molecular–Weight S–Nitroso Compounds and Their Thiols by High–Performance Liquid Chromatography and Gas Chromatography–Mass Spectrometry," *Analytical Biochemistry*, 270, pp. 231–241 (1999).

* cited by examiner

*Primary Examiner*—Paul J. Killos
(74) *Attorney, Agent, or Firm*—Fish & Neave; James F. Haley, Jr.; Min Wang

(57) ABSTRACT

SNACE derivatives as pharmacological active agents and pharmacological compositions containing these compounds, in particular for transdermal, oral, rectal and inhalational application, are described.

20 Claims, 7 Drawing Sheets

S-NITROSO- AND S-NITRO-N-ACYL-L-CYSTEINE ESTER DERIVATIVES AS PHARMALOGICALLY ACTIVE AGENTS AND PHARMACEUTICAL COMPOSITIONS CONTAINING SAID COMPOUNDS

CROSS-REFERENCE TO RELATED APPLICATIONS

This application is a continuation of co-pending International patent application PCT/EP00/03934, filed May 2, 2000, designating the United States and claiming priority from German patent application No. 199 19 941.8, filed Apr. 30, 1999.

TECHNICAL FIELD OF THE INVENTION

The invention relates to new S- nitroso- and S-nitro-N-acyl-L-cysteine ester derivatives (SNACE derivatives) as pharmacologically active agents and pharmacological compositions—in particular for transdermal application—which contain a SNACE derivative, for the prevention and treatment of a series of diseases including peripheral occlusive diseases, of the myocardial infarction, angina pectoris, the ischemic stroke, arteriosclerotic vascular changes, thrombosis (inhibition of the platelet aggregation), homocysteinemia, and impotentia coeundi, disfunctional miction, asthma bronchial, hypertonia, pulmonic hypertonia, diabetic nephropathy, mucoviscidosis, cancer and Alzheimer's disease.

BACKGROUND OF THE INVENTION

A variety of vasolidators are known which can be used for the treatment of hypertensive conditions, of angina pectoris, of impotentia coeundi, thrombosis and other diseases. These pharmaceutical compositions can be divided into different categories according to the mechanism of their primary effect. Three important groups of these pharmaceutical compositions are the inhibitors of the angiotensin converting enzyme (ACE), the organic nitrates and nitrogenmonoxide (NO) donors. Whereas neither ACE inhibitors nor the organic nitrates such as e.g. glyceryl trinitrate (GTN) are anti-aggregatory active substances which are clinically significant, some NO donors including the S-nitroso substances (RSNO) can have both an antihypetensive and an anti-aggregatory effect.

Contrary to the organic nitrates which are effective only after their metabolisation in the cells resulting in active intermediates, S-nitroso compounds have an effect without prior enzymatic activation either directly or after release of NO. Ignarro et al. (Biochem. Biophys. Acta, 631 (1980) 221–231) have shown that the S-nitroso-compounds of cysteine, glutathion, penicillamine and dithiothreitol are able to directly activate the soluble guanylate cylase (sGC). The effect of organic nitrates, sodium nitrite and nitroprusside sodium might possibly be due to the activation of the sGC after intermediate formation of S-nitroso substances from these substances and the thiols of the cells. The fact that the effect of organic nitrates depends on their metabolism and the thiol status of a cell could explain the development of tolerance towards organic nitrates. It was shown that S-nitroso substances such as the S-nitroso-N-acetyl penicillamines (SNAP) show no development of tolerance (Shaffer J E et al., J. Pharmacol. Exper. Ther. 260 (1992) 286–293) in vivo in an animal. It has been documented that the S-nitroso substances such as S-nitroso glutathion in vitro and in vivo have an anti-hypertensive and an anti-aggregatory effect in humans (De Belder et al., Cardiovasc. Res., 28 (1994) 691–694). For S-nitroso glutathion it was even shown that its anti-aggregatory component is by far more distinct than the anti-hypertensive one (De Belder et al., Cardiovasc. Res., 28 (1994) 691–694). For S-nitroso glutathion it was also shown that it reduces the rate of embolism in humans (Molloy et al., Circulation, 98 (1998) 1372–1375) and that this effect exceeds the one of acetylsalicylic acid and heparin.

The mechanisms of the anti-aggregatory effect of S-nitroso substances have not been clarified completely up until today. Apart from the cGMP-dependent mechanism, various cGMP-independent mechanisms have been discussed which are based on the influence of enzyme activitites or receptors by S-nitroso substances. It was shown, for example, that different S-nitroso substances and NO inhibit the enzymes glyceraldehyde-3-phophate-dehydrogenase (Padgett and Whorton, Am. J. Physiol. 269 (Cell Physiol. 38), (1995) C739–C749), phosphodiesterase (Maurice and Haslam R J, Molecular Pharmacol., 37 (1990) 671–681) and cyclooxygenase (Tsikas D et al., FEBS Lett., 442 (1999) 162–166).

The use of S-nitroso derivatives of ACE inhibitors and cysteine for the treatment of various diseases has been described by Loscalzo J and Cooke J (U.S. Pat. No. 5,025, 001, 1991) as well as Stamler J S and Loscalzo J (International Application Number PCT/US92/03008).

At the moment, no S-nitroso and S-nitro substances are authorised as medicaments.

The problem underlying the present invention is to provide SNACE derivatives as pharmaceutical compositions or pharmaceutically active agents. The SNACE derivatives of the invention are particularly suitable for pharmaceutical preparations for the transdermal application since—absorbed through the skin and after resorption—they themselves or as metabolites (e.g. of hydrolases, deacylases) are effective as pro-drug directly or indirectly.

Thus, S-nitroso and S-nitro-N-acyl-L-cysteine ester derivatives with the general formula I

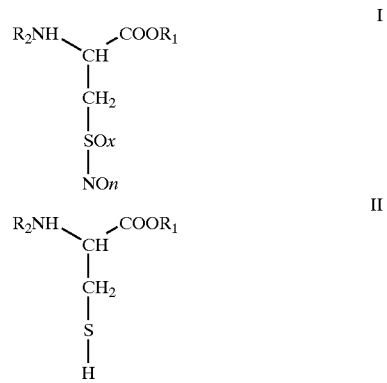

are subject matter of the invention, wherein n=1 or N=2, x=0, 1 or 2, $R_1$ is an alkyl group ($C_{1-22}$) and $R_2$ is an acyl group ($C_{2-22}$) or O-acetylsalicyl group or an alkyl group ($C_{1-22}$) as pharmacologically active agents.

SUMMARY OF THE INVENTION

S-Nitroso and S-nitro-N-acyl-L-cysteine ester derivatives with the general formula I.

DETAILED DESCRIPTION OF THE INVENTION

Alkyl and acyl groups with up to 6 carbon atoms are preferred.

The methyl, ethyl, n-propyl and tert-butyl group are examples of alkyl groups. The acetyl priopionyl and tert-butyryl and O-acetylsalicyl group are examples of acyl groups.

The particularly preferred alkyl and acyl groups are the ethyl, acetyl and O-acetylsalicyl group due to the fact that their cleavage products ethanol, acetic acid and O-acetylsalicylic acid or salicylic acid are non-toxic.

The pharmacologically effective group of the compounds with the general formula I is the S-nitroso group (—S—N=O) or the S-nitro group (S—$NO_2$). The alkyl and acyl groups and the substituents at the sulphur of the compounds with the general formula I primarily influence the physico-chemical properties, e.g. the penetration rate in the skin, and not so much their pharmacological activity.

The production of the compounds of the general formulae I and II is carried out according to methods known per se by esterification of the carboxyl group of cysteine and N-acylation or N-alkylation of the amino group of cysteine. Esters are produced e.g. by use of 3 M HCl in the corresponding water-free alcohols. N-acyl derivatives are produced e.g. by use of anhydrides of the corresponding carbon acids. N-alkyl derivatives are produced e.g. by use of alkyl halides. The compounds of the general formula II are the precursors of the corresponding compounds with the general formula I. The nitrosylation of the thiol group of cysteine derivatives of the general formula II takes place in hydrochloric acid-acidic solution by stoichiometric amounts of sodium nitrite (Tsikas et al., Anal. Biochem. 244 (1997) 208–220). The nitration of the thiol group of compounds of the general formula II takes place e.g. by use of nitronium tetrafluoroborate (Balazy et al., J. Biol. Chem. 273 (1998) 32009–32015).

Alternatively, the production of the compounds of the general formula I (n=1 or 2 and x=0) by S-transnitrosylation or S-transnitration of the thiol group of the corresponding cysteine derivative of the general formula II takes place by means of e.g. S-nitrosoglutathion or S-nitroglutathion (Tsikas et al., Anal. Biochem. 270 (1999) 231–241). This method can also be used for the in situ production of the compounds of the general formula I in the pharmacological composition. The SNACE derivatives with x=1 and x=2 are produced from the corresponding derivatives with x=0 by oxidation e.g. hydrogen peroxide.

The compounds with the general formula I can be used for the prevention of arteriosclerosis, for the treatment of hypertonia and pulmonic hypertonia, for the prevention and treatment of blood circulation disorders, e.g. of the brain, the heart and the extremities, for the inhibition of the platelet aggregation (thrombocyte aggregation), for the treatment of impotentia coeundi and for the treatment of asthma bronchiale, for the treatment of cystic fibrosis (mucoviscidosis) and of rejection reaction with transplants as well as cancer, homocysteinemia and for lipid reduction. Typical examples of disorders of the blood circulation of the brain are transitory cerebral ischemia, sudden deafness, dizziness due to circulation disorders and ischemic stroke. Typical examples of disorders of the blood circulation of the heart are angina pectoris and heart attack. Typical examples of blood circulation disorders of the extremities are peripheral artery blood circulation disorders with arteriosclerosis, M. Burgers and M. Raynaud as well as Raynaud's syndrome.

Apart from the transdermal application, also the oral, rectal, intravenous or intra-arterial application as well as the inhalational application also in liposomes, micro-emulsions and micro-capsules can be considered for the compounds of the general formula I.

The production of pharmacological compositions takes place according to standard methods. For the production of pharmacological compositions for the transdermal application, the compounds of the general formula I can be used in the absence or in the presence of the corresponding compounds of the general formula II in a gel base, ointment base or a liquid base with or without different solution mediators, penetration accelerators as well as stabilisers. Sprays, tubes, ampuls as well as single portions can be used as primary packing material. After application onto the skin or with additional occlusion dressing, the active agent is absorbed.

Optionally, the compounds with the general formula I can also be applied with stabilisers as well as solution mediators on a plaster.

EXAMPLE 1

A. Production of S-nitroso-N-acetylcysteine ethyl ester
I. Production of the precursor N-acetylcysteine ethyl ester (NACET)

L-cysteine ethyl ester hydrochloride (9.2 g, 50 mmol) is suspended in methylene chloride (100 ml). The suspension is alkalised with saturated $NaHCO_3$ (25 ml) and with 2 M NaOH (20 ml). After the phase separation, the organic phase is decanted and the remaining aqueous phase is extracted with methylene chloride (30 ml). The organic phases are combined, dried over aqueous-free $Na_2SO_4$ and filtered. Acetic acid anhydride is added to the clear solution (in total: 4 g, 39.2 mmol) until complete (controlled with thin layer chromatography: Silica, diethylether: methanol, 9/1, v/v, using cerammonium nitrate for detection). The solvent is concentrated until dry and the residue is cromatographed on silica with diethylether for elution. All the operations are carried out at room temperature in a argon atmosphere. White crystals (6.2 g, melting point: 44.1–44.5° C.) are the result. The compound is identified by means of mass spectronomy, $^1$H-NMR, IR and polarimetry as N-acetylcysteine ethyl ester ($C_7H_{13}NO_3S$, MG 191).

II. Production of S-nitroso-N-acetylcysteine ethyl ester (SNACET)

A mixture of N-acetylcysteine ethyl ester (9.55 mg, 50 µmol) and sodium nitrite (3.45 mg, 50 µmol) is produced in deoxygenated, distilled, ice-cold water. Deoxygenated, ice-cold 5 M HCl solution (12 µl, 60 µmol) is added to this solution. Straight after the acidulation, the solution turns red. The resulting substance was identified as S-nitroso-N-acetylcysteine ethyl ester ($C_7H_{12}N_2O_4S$, MG 220) by means of MS, $^1$H-NMR, IR and spectrophotometry (molar absorption coefficient of 780 $M^1cm^{-1}$ at a wave length of 338 nm of the maximum absorption). The purity of the substance is determined to be >99% by means of reverse phase high pressure liquid chromatography (HPLC, detection at 338 nm).

B. Production of S-nitroso-N-(O-acetylsalicyl)cysteine ethyl ester
I. Production of the Precursor N-(O-acetylsalicyl)cysteine ethyl ester (ASS-CET)

Triethylamine (510 mg) is added to cysteine ethyl ester hydrochloride (925 mg, 5 mmol) in tetrahydrofuran (30 ml) while ice-cooling for 2 hours. A solution of acetylsalicylacid anhydride (1.71 g, 5 mmol) in tetrahydrofuran (10 ml) is added to the resulting suspension and the mixture is stirred for 2 hours. The reaction mixture is diluted with water and the reaction products are extracted with diethylether. Subsequently, the extract is washed and dried over aqueous-free MgSO$_4$. The solvent is concentrated until dry and the residue is chromatograhped on silica with diethylether/petrolether (1/1, v/v) for elution. All the operations were carried out at room temperature in an argon atmosphere. White crystals (950 mg, melting point: 76–77° C.) were the result. The compound is identified as N—(O-acetylsalicyl)cysteine ethyl ester (C$_{14}$H$_{17}$NO$_5$S, MG 311) by means of mass spectronomy, $^1$H-NMR, IR and polarimetry.

II. Production of S-nitroso-N-(O-acetylsalicyl)cysteine ethylester (ASS-SNCET)

A mixture of N-(O-acetylsalicyl)cysteine ethyl ester (15.6 mg, 50 µmol) and sodium nitrite (3.45 mg, 50 µmol) is produced in deoxygenated, distilled, ice-cold water. A deoxygenated, ice-cold 5 M HCl solution (12 µl, 60 µmol) is added to this solution. Straight after the acidification, the solution turns red. The resulting substance was identified as S-nitroso-N-(O-acetylsalicyl)cysteine ethyl ester (C$_{14}$H$_{16}$N$_2$O$_6$S, MG 340) by means of MS, $^1$H-NMR, IR and spectrophotometry (molar absorption co-efficient of 800 M$^{-1}$cm$^{-1}$ at a wave length of 338 nm of the maximum absorption). The purity of the substance is determined to be >99% by means of reverse phase high pressure liquid chromatography (HPLC, detection at 338 nm as well as 254 nm).

C. Alternative Production of S-nitroso-N-acetylcysteine ethyl ester and S-nitroso-N-(O-acetylsalicyl)cysteine ethyl ester from GSNO and NACET or ASS-CET by S-transnitrosylation in a Two-phase System Solutions of NACET (9.55 mg, 50 µmol) and ASS-CET (15.6 mg, 50 µmol) are produced in ice-cold methylene chloride (2 ml each). Two solutions of S-nitroso-L-glutathion 0.5 H$_2$O (GSNO; 20.6 mg each, 60 µmol each) are produced in ice-cold deoxygenated water (1 ml each). The NACET and ASS-CET solutions are mixed intensively with the GSNO solution for 5 min by means of a vortex mixer. The reddish aqueous phases lose their colour, while the organic phases turn reddish. That is an indication for the conversion from GSNO into SNACET and ASS-SNCET. Methylene chloride is concentrated completely using nitrogen. The result are deep-red oily liquids which form red crystals after storage at −20° C. The purity of the substances was determined to be >99% each by means of reverse phase high pressure liquid chromatography (HPLC, detection at 338 nm); according to HPLC no GSNO was present in SNACET or ASS-SNCET.

The production of the corresponding S-nitro derivatives from S-nitroglutathion takes place analogously.

EXAMPLE 2

A. Relaxation of the Human Corpus Cavernosum in vitro by Means of S-nitroso-N-acetylcysteine ethyl ester, S-nitroso-N-(O-acetylsalicyl)cysteine ethyl ester and Their Metabolites S-nitroso-N-acetylcysteine ethyl ester (SNACET), S-nitroso-N-(O-acetylsalicyl) cysteine ethyl ester (ASS-SNCET) and their metabolites S-nitroso-N-acetylcysteine (SNAC) and S-nitroso-cysteine ethyl ester (SNCET) relax human Corpus Cavernosum in vitro in a concentration-dependent manner (FIG. 1a).

B. Relaxation of the Human Arteria Mammaria in vitro by S-nitroso-N-acetylcysteine ethyl ester and S-nitro-N-acetylcysteine ethyl ester S-nitroso-N-acetylcysteine ethyl ester (SNACET) and S-nitro-N-acetylcysteine ethyl ester (SNO$_2$-ACET) relax human arteria mammaria in vitro in a concentration-dependent manner (FIG. 1b).

The relaxing effect of SNACE derivatives on the human Corpus Cavernosum and the human arteria mammaria shows that pharmacological compositions containing SNACE derivatives for the treatment of impotentia coeundi and of blood circulation disorders of the heart are suitable as pharmacologically active agents.

EXAMPLE 3

Penetration of S-nitroso-N-acetylsysteine ethyl ester (SNACET) by Human *Tunica albuginea in vitro*

Part of *Tunica albuginea* which has just been prepared is fixed in a Franz' cell. The active surface is 1.77 cm$^2$. The acceptor phase (10 ml) consists of Hank's buffer (pH 7.4), human albumin (30 g/l), penicillin G (100 units) and streptomycin (10 µg) and is stirred with a magnetic stirrer at a constant rotation speed. The penetration is started by application of solutions of SNACET in dimethyl sulphoxide at various concentrations (0.25 ml) on the part of the skin. At various points in time, samples are taken from the acceptor phase and the concentration of the sum from SNACET and its metabolites is determined. In the acceptor phase, unmodified SNACET and other metabolites including nitrite are detected. FIG. 2 shows that SNACET penetrates the *Tunica albuginea*. The penetration rate and the amount of the penetrated SNACET and their metabolites in the acceptor phase depend on the amount of SNACET applied onto the *Tunica albuginea*. The lag time is approximately 20 min. In the linear region, the penetration rates are 1.0, 2.5 or 5.0 µmol SNACET/hour.

Similar results were achieved with complete skin of chest or belly of healthy donors.

The penetration of SNACE derivatives by means of *Tunica albuginea* and with complete skin shows that the application of pharmacological compositions containing SNACE derivatives onto the skin for the resorption of the drug via the skin which causes the SNACE derivatives and their metabolites to reach target organs and become therapeutically active there.

EXAMPLE 4

Hypotensive Effect of SNACET in vivo in the Rat

S-nitroso-N-acetylcysteine-ethylester (SNACET) is applied i.v. to a male, anaesthetised Sprague Dawley rat which has a weight of 400 g. Before and after the infusion, the average artery blood pressure is taken continuously. FIG. 3 shows that immediately after start of the infusion of SNACET, the average artery blood pressure decreases in dependence on the infusion rate.

EXAMPLE 5

Inhibition of the Aggregation of Human Blood Platelets in vitro by Means of S-nitroso-N-acetylcysteine ethyl ester (SNACET) and S-nitroso-N-(O-acetylsalicyl)cysteine ethyl ester (ASS-SNCET)

Collagen-induced (2 µg/ml) aggregation and thromboxane synthesis in human blood platelets which have been washed are inhibited by SNACET in a concentration-dependent manner (FIG. 4a). The IC$_{50}$s for the inhibition of the platelet aggregation and the thromboxane synthesis by SNACET are determined at 1 and 0.5 µM. Collagen-induced (2 µg/ml) aggregation of human blood platelets that have been washed is inhibited by ASS-SNCET in a concentration-dependent manner (FIG. 4b). The IC$_{50}$ for the inhibition of the platelet aggregation by ASS-SNCET is determined at 2 µM (FIG. 4b).

EXAMPLE 6

In vivo Metabolism of Orally Applied $^{15}$N-marked S-nitroso-N-acetylcysteine ethyl ester ($^{15}$N-SNACET) in the Rat A male Sprague Dawley rat weighing 480 g is orally given 17.5 mg of $^{15}$N-marked S-nitroso-N-acetylcysteine ethyl ester ($^{15}$N-SNACET) per kg body weight, dissolved in 1 ml of a 10% (w/v) glucose solution in drinking water. Before and up to 24 hours after application, urine is collected and the $^{15}$N-concentration of nitrate, nitrite and S-nitroso metabolites of $^{15}$N-SNACET is determined by means of GC-MS. FIG. 5 shows that neither $^{15}$N-SNACET no other S-[$^{15}$N]nitroso-containing metabolites are secreted into the urine. $^{15}$N-nitrate is identified as the main metabolite of $^{15}$N-SNACET. $^{15}$N-nitrite is also secreted into the urine. The highest $^{15}$N-concentration is measured in the urine sample collected within the first two hours. The $^{15}$N-concentration in the urine 24 hours after the administration of $^{15}$N-SNACET is insignificantly higher than the natural occurrence of $^{15}$N.

The secretion of nitrate in the urine of the rat after oral application of SNACET illustrates that pharmacological compositions containing SNACE derivatives administered orally are resorbed quickly and—metabolised as nitrates— secreted via the urine.

BRIEF DESCRIPTION OF THE DRAWINGS

FIG. 1 a. Relaxation of the human Corpus Cavernosum in vitro by S-nitroso-N-acetylcysteine-ethylester (SNACET), S-nitroso-N-(O-acetylsalicyl)cysteine ethyl ester (ASS-SNCET) and their metabolites SNCET and SNAC.

Figure 1A:
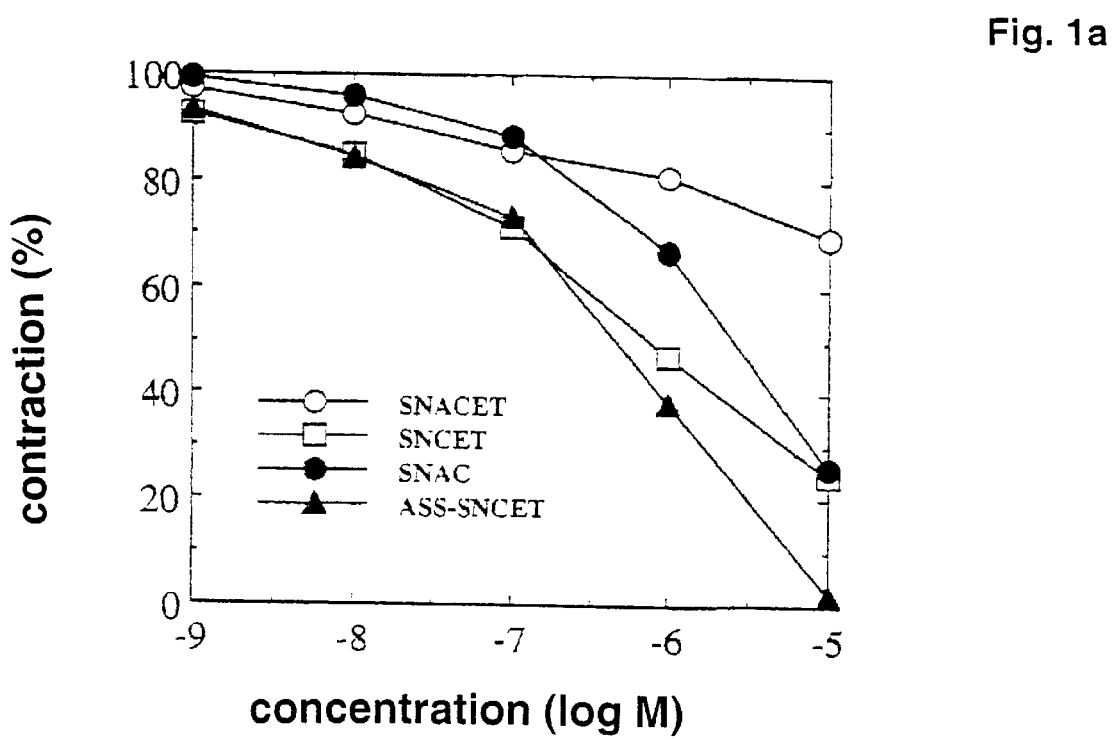
Figure 1B:
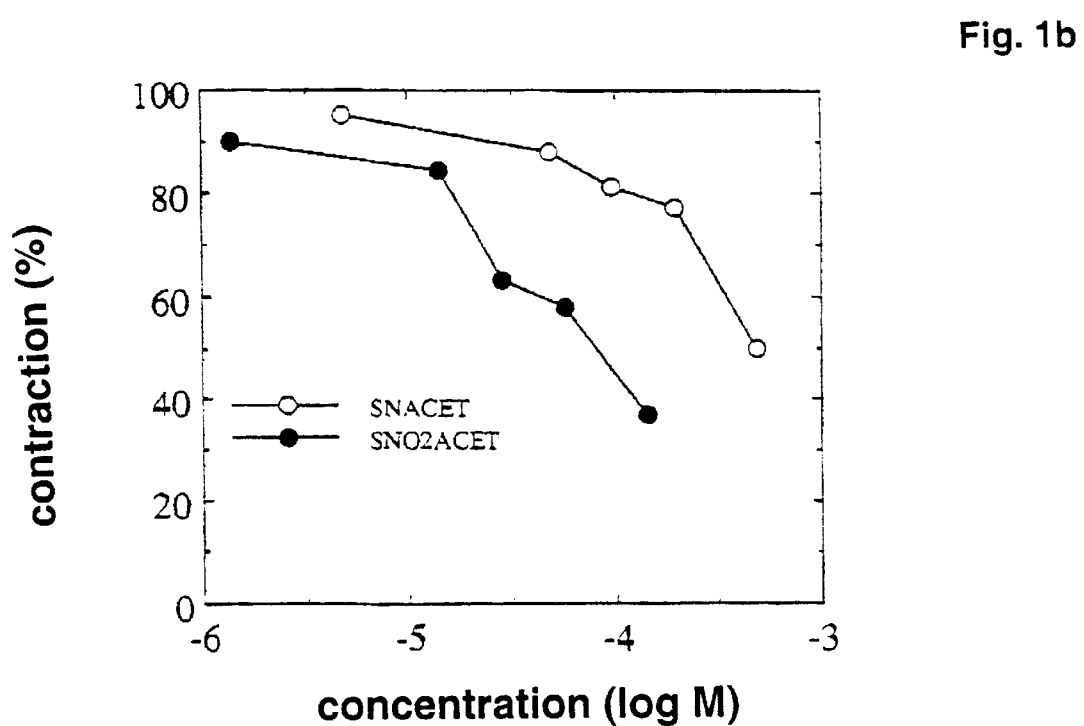
Figure 2:
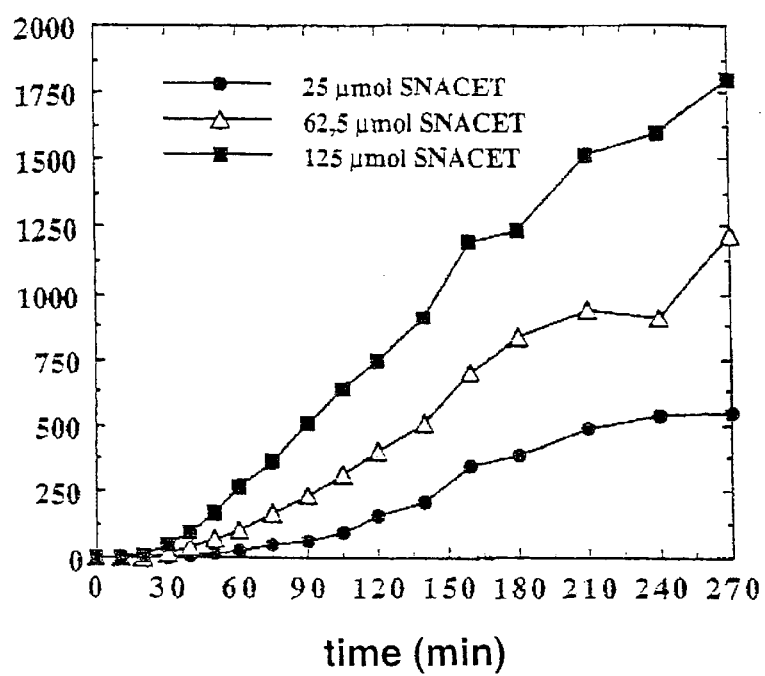
Figure 3:
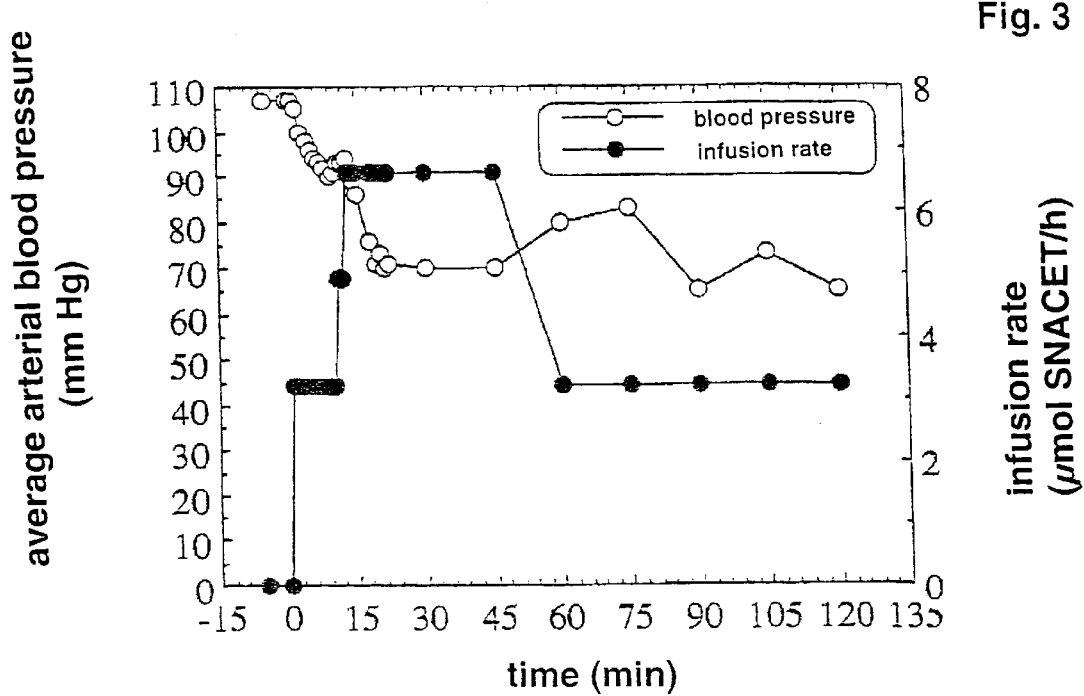
Figure 4A:
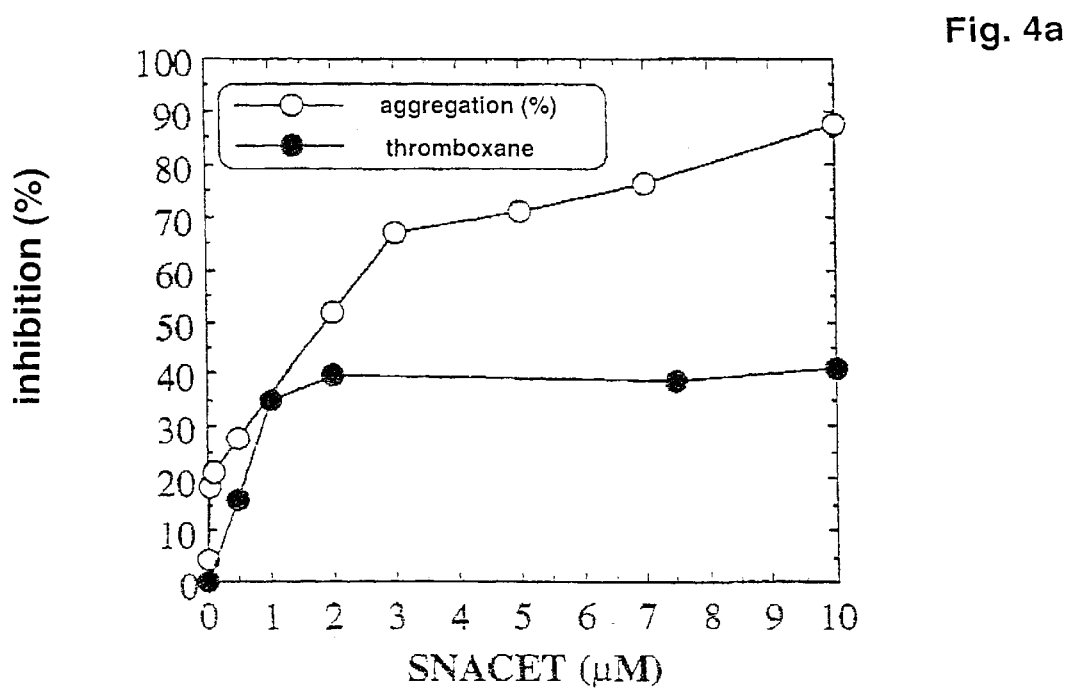
Figure 4B:
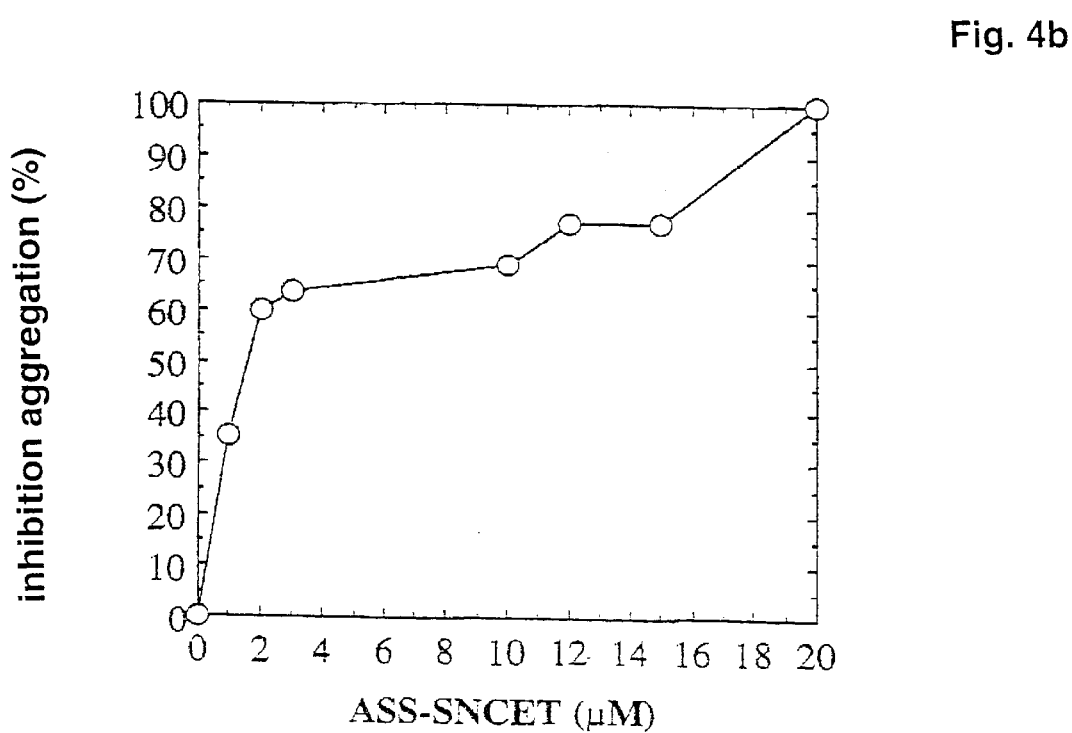
Figure 5:
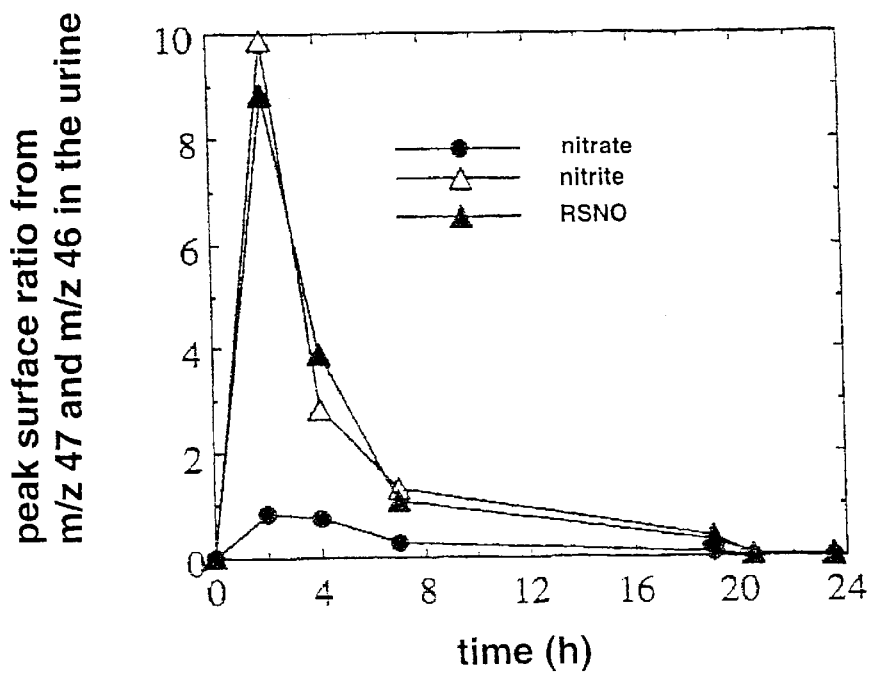

b. Relaxation of the human arteria mammaria in vitro by S-nitroso-N-acetylxysteine ethyl ester (SNACET) and S-nitro-N-acetylcysteine ethyl ester (SNO$_2$ACET).

FIG. 2

Penetration of S-nitroso-N-acetylcysteine ethyl ester (SNACET) by human Tunica albuginea in vitro in a Franz' cell. Three different amounts dissolved in dimethyl sulphoxide (250 µl each) were applied (see Legend).

FIG. 3

Hypotensive effect of SNACET in vivo in the rat. SNACET was applied i.v. with the infusion rates stated.

FIG. 4 a. Inhibition of the collagen-induced (2 µg/ml) aggregation of human blood platelets that have been washed and the thromboxane synthesis in the platelets in vitro by S-nitroso-N-acetylcysteine ethyl ester (SNACET).

b. Inhibition of the collagen-induced (2 µg/ml) aggregation of human blood platelets in vitro that have been washed by S-nitroso-N-(O-acetylsalicyl)cysteine ethyl ester (ASS-SNCET). The values are average values from analyses with platelets of four healthy subjects.

FIG. 5

Metabolism of orally applied $^{15}$N-marked S-nitroso-N-acetylcysteine-ethylester (17.5 mg/kg body weight) in a rat. $^{15}$N-concentration of nitrate, nitrite and for the sum of $^{15}$N-marked S-nitroso-N-acetylcysteine ethyl ester and its metabolites collected in the urine before and up to 24 hours after the application.

What is claimed is:

1. A compound of the general formula I

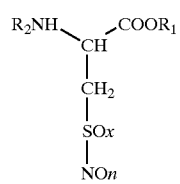

I wherein n is 1 or 2, x is 0, 1 or 2, $R_1$ is an alkyl group ($C_{1-22}$) and $R_2$ is an acyl group ($C_{2-22}$) or an O-acetylsalicyl group, with the exclusion of S-nitroso-N-acetylcysteine methyl ester.

2. The compound according to claim 1, wherein $R_1$ is an ethyl group, $R_2$ an acetyl group, n is 1 and x is 0.

3. The compound according to claim 2, wherein $R_1$ is an ethyl group, $R_2$ an O-acetylsalicylyl group, n is 1 and x is 0.

4. A pharmaceutical composition comprising a compound of the general formula II

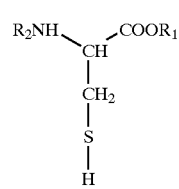

II and S-nitrosoglutathion (GSNO) or S-nitroglutathion (GSNO$_2$) as pro drug complexes from which the compound of the general formula I is generated in situ:

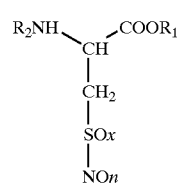

I wherein n is 1 or 2, x is 0, $R_1$ is an alkyl group ($C_{1-22}$) and $R_2$ is an acyl group ($C_{2-22}$) or an O-acetylsalicyl group.

5. A pharmaceutical composition comprising a compound according to any one of claims 1 to 4.

6. The pharmaceutical composition according to claim 5, wherein said composition is effective for the prevention and treatment of blood circulation disorders.

7. The pharmaceutical composition according to claim 5, wherein said composition is effective for the treatment of impotentia coeundi.

8. The pharmaceutical composition according to claim 5, wherein said composition is effective for the inhibition of the platelet aggregation.

9. The pharmaceutical composition according to claim 5, wherein said composition is effective for the treatment of asthma bronchiale.

10. The pharmaceutical composition according to claim 5, wherein said composition is effective for the treatment of mucoviscidosis.

11. The pharmaceutical composition according to claim 5, wherein said composition is effective for the treatment of homocysteinemia.

12. The pharmaceutical composition according to claim 5, wherein said composition is effective for the treatment of cancer.

13. The pharmaceutical composition according to claim 5, wherein said composition is effective for the treatment of Alzheimer's disease.

14. The pharmaceutical composition according to claim 5, wherein said composition is effective for lipid reduction.

15. The pharmaceutical composition according to claim 5, wherein said composition is effective used for the prevention and the treatment of arteriosclerotic vessel changes, Angina pectoris, heart attack, stroke, or peripheral blood circulation disorders.

16. The pharmaceutical composition according to claim 5, wherein said composition is effective for the treatment of hypertonia or pulmonic hypertonia.

17. The pharmaceutical composition according to claim 5, wherein said composition is effective for the treatment of rejection reactions with transplants.

18. The pharmaceutical composition according to claim 5, wherein said composition is effective for intravenous or intra-artery application.

19. The pharmaceutical composition according to any one of claims 4 to 17 for transdermal, oral, rectal or inhalational application.

20. The pharmaceutical composition according to any one of claims 4 to 18 in form of liposomes, micro-capsules or a micro emulsion or as transdermal therapeutic system (TTS).

* * * * *